United States Patent [19]

Alaimo et al.

[11] 3,931,168

[45] Jan. 6, 1976

[54] CINNAMAMIDOHYDANTOINS

[75] Inventors: Robert J. Alaimo, Norwich; Christopher J. Hatton, Earlville, both of N.Y.

[73] Assignee: Morton-Norwich Products, Inc., Norwich, N.Y.

[22] Filed: Aug. 1, 1974

[21] Appl. No.: 493,681

[52] U.S. Cl. ........ 260/240 J; 260/309.5; 260/340.5; 260/465 D; 260/515 A; 260/544 M; 260/568; 260/569; 260/240 K; 424/273
[51] Int. Cl.² .................................. C07D 233/80
[58] Field of Search .......... 260/240 J, 240 K, 309.5, 260/240 D

[56] References Cited
UNITED STATES PATENTS

| | | | |
|---|---|---|---|
| 3,182,058 | 5/1965 | Conover | 260/309.5 |
| 3,830,805 | 8/1974 | Pilgram | 260/309.5 |
| 3,835,128 | 9/1974 | Bracha et al. | 260/240 J |

OTHER PUBLICATIONS

Wagner et al., Synthetic Organic Chemistry, John Wiley & Sons, Inc., N.Y., N.Y., 1953, p. 566.

*Primary Examiner*—Arthur P. Demers
*Attorney, Agent, or Firm*—Anthony J. Franze

[57] ABSTRACT

A series of cinnamamidohydantoins are useful as anthelmintic agents.

12 Claims, No Drawings

CINNAMAMIDOHYDANTOINS

This invention is concerned with chemical compounds. More particularly, it is concerned with a series of cinnamamidohydantoins of the formula:

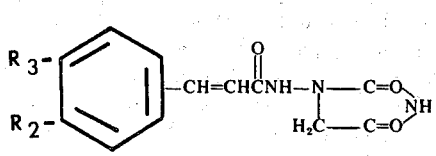

wherein $R_2$ is a member of the group consisting of hydrogen, chloro, fluoro and trifluoromethyl; $R_3$ is a member of the group consisting of hydrogen, chloro, fluoro, methyl, ethyl, and cyano; and $R_2$ and $R_3$ taken together are methylenedioxy.

The members of this series are effective anthelmintic agents. They are particularly inimical to *Syphacia obvelata* a pinworm whose sensitivity to oxyuricidal agents is known to be substantially the same as that for the species *Enterobius vermicularis* a causative agent of pinworm infection in human beings. Thus when administered per os suspended in a suitable vehicle such as an aqueous solution of carboxymethyl cellulose to mice harboring *Syphacia obvelata* in a dose of about 100 mg/kg b.i.d. for 5 days eradication of worms to the extent of from 70 to 100% is achieved.

The method which is currently preferred for preparing members of this series of compounds consists in reacting the appropriate cinnamoyl chloride with 1-aminohydantoin in the presence of an acid acceptor such as pyridine advantageously under the influence of heat.

In order that this invention may be readily available to and understood by those skilled in the art the following examples are appended.

EXAMPLE I

1-(3,4-Dichlorocinnamido)hydantoin to 3,4-dichlorocinnamic acid (22 g, 0.1 mole) was added dropwise thionyl chloride (70 ml, 1 mole). After the addition was complete, the mixture was stirred for 1/2 hr, then the excess $SOCl_2$ evaporated in vacuo. The residue was treated with benzene (50 ml) stirred, then evaporated in vacuo, this was repeated again and finally to the residue was added a suspension of 1-aminohydantoin hydrochloride (15.2 g, 0.1 mole) in pyridine (200 ml). The reaction mixture was heated on the steam bath for 3 hrs, then treated with Darco and filtered. The pyridine solution was poured onto 1000 ml of ice and the precipitated product (28 g 89%) recrystallized from methanol/dimethylformamide/$H_2O$ to give crystals which melted at 286°–288°.

Anal. Calcd. for $C_{12}H_9Cl_2N_3O_3$: C, 45.88; H, 2.89; N, 13.38. Found: C, 46.03; H, 3.03; N, 13.12.

EXAMPLE II

1-Cinnamamidohydantoin

To a pyridine solution (500 ml) of 1-aminohydantoin hydrochloride (50 g, 0.3 mole) was added cinnamoyl chloride (53 g, 0.3 mole). The stirred mixture was heated on the steam bath for 5 hours, then poured into ice water. After standing overnight, the precipitated product was removed by filtration and washed thoroughly with water. After drying, the crude white product weighed 60 g (74%). Several recrystallizations from methanol provided analytical material which melted at 276°–278°.

Anal. Calcd. for $C_{12}H_{11}N_3O_3$: c, 58.77; H, 4.52; N, 17.14. Found: C, 58.80; H, 4.59; N, 16.97.

EXAMPLE III

1-(3-Chloro-4-methylcinnamamido)hydantoin

To 3-chloro-4-methylcinnamic acid (50 g, 0.25 mole) was added dropwise $SOCl_2$ (140 ml). The mixture was heated under reflux for 45 min. after the addition was complete. After stirring at room temperature for 1 hour the $SOCl_2$ was removed in vacuo. Dry benzene was added and then removed in vacuo. The acid chloride residue was treated with 1-aminohydantoin hydrochloride (42 g, 0.275 mole) in 350 ml of pyridine, then heated under reflux for 2 hr. After cooling slightly, the reaction mixture was poured into a mixture of 200 ml of con HCl and 1500 ml of ice. After standing overnight the product was removed by filtration and washed with $H_2O$. Recrystallization from $CH_3NO_2$ provided analytical material which melted at 271°–273° (28 g, 38%).

Anal. Calcd. for $C_{13}H_{12}ClN_3O_3$: C, 53.16; H, 4.12; N, 14.31. Found: C, 52.82; H, 4.11; N, 14.27.

EXAMPLE IV

1-(4-Chlorocinnamamido)hydantoin

To 4-chlorocinnamic acid (46 g, 0.25 mole) was added dropwise $SOCl_2$ (140 ml). The mixture was heated under reflux for 45 minutes after the addition was complete. After stirring at room temperature for 1 hour the $SOCl_2$ was removed in vacuo. Dry benzene was added and then removed in vacuo. The acid chloride residue was treated with 1-aminohydantoin hydrochloride (42 g, 0.275 mole) in 350 ml of pyridine, then heated under reflux for 2 hrs. After cooling slightly, the reaction mixture was poured into a mixture of 200 ml of con HCl and 1500 ml of ice. After standing overnight the product was removed by filtration and washed with $H_2O$. Recrystallization from NaOH/dimethylformamide ($H_2O$) provided analytical material which melted at 230°–235° (25 g, 36%).

Anal. Calcd. for $C_{12}H_{10}ClN_3O_3$: C, 51.53; H, 3.60; N, 15.03 Found: C, 51.49; H, 3.58; N, 14.89.

EXAMPLE V

1-(3,4-Methylenedioxycinnamamido)hydantoin

A stirred quantity of 3,4-methylenedioxycinnamic acid (38 g, 0.2 mole) was treated dropwise with 200 ml of $SOCl_2$. After the addition was complete the reaction mixture was stirred at room temperature for 1 hour and heated at reflux for 2 hours. The reaction solution was distilled to remove the excess $SOCl_2$. The tan residue, after treatment with 100 ml of dry benzene, was distilled again. The residue remaining was treated with a mixture of 1-aminohydantoin hydrochloride (30 g, 0.2 mole) in 400 ml of pyridine. After the addition was complete the reaction mixture was heated at reflux for 3 hours. The reaction solution was poured into 4 l. of water to give a precipitate. After standing at room temperature overnight the solid was filtered and washed in water to give 47 g (81%) of product.

An analytical sample was prepared by two recrystallizations from $CH_3CN$ m.p. 258°–260°.

Anal. Calcd. for $C_{13}H_{11}N_3O_5$: C, 53.98; H, 3,83; N, 14.53. Found: C, 53.90; H, 3.83; N, 14.43.

EXAMPLE VI 1-(4-Chloro-3-trifluoromethylcinnamamido)hydantoin

A stirred mixture of 4-chloro-3-trifluoromethylcinnamic acid (50 g, 0.2 mole) in 200 ml of $SOCl_2$ was heated at reflux for 2 hours. The excess $SOCl_2$ was removed in vacuo and the residue flushed with dry benzene. The residue was treated with a mixture of 1-aminohydantoin hydrochloride (30 g, 0.2 mole) in 400 ml of pyridine. The reaction mixture was heated at reflux for 3 hours; then poured into ice/HCl. The crude residue (74 g, 100%) was recrystallized from $CH_3NO_2$ (Darco) to give an analytical sample melting at 270°–273°.

Anal. Calcd. for $C_{13}H_9ClF_3N_3O_3$: C, 44.91; H, 2.61; N, 12.09. Found: C, 44.98; H, 2.73; N, 11.75.

EXAMPLE VII 1-(p-fluorocinnamamido)hydantoin

A mixture of p-fluorocinnamic acid (36 g, 0.22 mole) in $SOCl_2$ (75 ml) was heated under reflux with stirring for 1 hour. The excess $SOCl_2$ was removed in vacuo and the residue fluxhed with benzene. To the resulting acid chloride was added 1-aminohydantoin hydrochloride (39 g, 0.26 mole) and 250 ml of pyridine and the resulting reaction mixture was heated on the steam bath for 3 hours. The mixture was poured onto HCl/ice and the product allowed to crystallize.

Recrystallization from $CH_3NO_2$ provided analytical material which melted at 241°–243°. Yield: 35 g, 62%.

Anal. Calcd. for $C_{12}H_{10}FN_3O_3$: C, 54.75; H, 3.83; N, 15.97. Found: C, 54.73; H, 3.85; N, 15.97.

EXAMPLE VIII 1-(3-Chloro-4-ethylcinnamamido)hydantoin

3-Chloro-4-ethylcinnamic acid (50 g, 0.24 mole) in $SOCl_2$ (100 ml) was heated under reflux for about 1 hour. The excess $SOCl_2$ was removed in vacuo and the residue flushed with benzene. The acid chloride was treated with 1-aminohydantoin hydrochloride (40 g, 0.26 mole) and pyridine (300 ml) and the reaction mixture heated on a steam bath for 4 hours. The reaction mixture was poured onto HCl/ice to precipitate the product. (40 g, 55%). Several recrystallizations from $CH_3NO_2$ provided analytical material which melted at 231°–234°.

Anal. Calcd. for $C_{14}H_{14}ClN_3O_3$: C, 54.64; H, 4.59; N, 13.66. Found: C, 54.22; H, 4.65; N, 13.91.

EXAMPLE IX 1-(p-Cyanocinnamaido)hydantoin

A. p-Cyanocinnamic Acid

A stirred mixture of p-cyanobenzaldehyde (50 g, 0.38 mole) malonic acid (47 g, 0.45 mole) and 4 ml of piperidine in 150 ml of pyridine was heated on a steam bath for 2 hours. The reaction solution was poured into a mixture of 220 ml of concentrated hydrochloric acid and 380 g of ice to give after filtration and water wash 78 g (45%) m.p. 240°. The crude intermediate was used in part B without further purification.

B. 1-(p-Cyanacinnamamido)hydantoin

To 43 g (0.25 mole) of p-cyanocinnamic acid was added dropwise thionyl chloride (250 ml) followed by heating at reflux for 2 hours. This excess thionyl chloride was removed in vacuo and the residue remaining flushed with dry benzene. The reaction residue was chilled on an ice bath followed by the rapid addition of 1-aminohydantoin hydrochloride (38 g. 0.25 mole). To the cold reaction mixture was added dropwise pyridine (450 ml). After the addition was complete the cold reaction mixture was heated on a steam bath for 3 hours then poured into a 4 l. of HCl/ice. Upon standing at room temperature overnight the acidic reaction mixture was filtered and washed with water to yield 45 g. The solid melted at 290°–292°. An analytical sample was prepared by one recrystallization from $CH_3NO_2$ (DARCO) m.p. 304°–305°.

Anal. Calcd. for $C_{13}H_{10}N_3O_3$: C, 57.77; H, 3.73; N, 20.74. Found: C, 57.73; H, 3.76; N, 20.73.

EXAMPLE X 1-(m-Fluorocinnamanido)hydantoin

A. m-Fluorocinnamic acid

A stirred mixture of m-fluorobenzaldehyde (112 g, 0.9 mole) malonic acid (120 g, 0.9 mole) and 2.5 ml of piperidine in 500 ml of pyridine was heated on a steam bath for 4 hours. The reaction solution was poured into a mixture of 550 ml of concentrated hydrochloric acid and 1 kg of ice to give after filtration and water wash 100 g (66.5%). The crude intermediate was used without further purification in part B.

B. 1-(m-Fluorocinnamamido)hydantoin

To 99.5 g (0.6 mole) of m-fluorocinnamic acid was added dropwise thionyl chloride (600 ml) followed by heating at reflux for 2 hours. The excess thionyl chloride was removed in vacuo and the residue remaining flushed with dry benzene. The reaction residue was chilled on an ice bath followed by the rapid addition of 1-aminohydantoin hydrochloride (91 g, 0.6 mole). To the cold reaction mixture was added dropwise pyridine (600 ml). After the addition was complete the cold reaction mixture was heated on a steam bath for 3 hours then poured into 6 l. of HCl/ice. Upon standing at room temperature overnight the acidic reaction mixture was filtered and washed with water to give 116 g (73.5%) which after recrystallization from $CH_3NO_2$ melted at 294°–296°.

EXAMPLE XI 1-(3-Chloro-4-fluorocinnamamido)hydantoin

A. To a stirred mixture of 3-chloro-4-fluoraniline (114 g, 0.78 mole) in 155 ml of water was added dropwise 177 ml of concentrated hydrochloric acid. The warm reaction mixture was cooled to room temperature and then cooled further with the addition of 310 g of ice. The reaction mixture was chilled and maintained at −5° to 5° by means of a salt/ice bath. To the cold reaction mixture was added dropwise a solution of sodium nitrite (55 g, 0.8 mole) in 78 ml of water. After the addition was complete the cold reaction mixture was stirred for 15 minutes followed by the addition of fused sodium acetate (69 g) in 109 ml of water to a Congo red indicator. The diazonium salt mixture was kept at −5° to 5° for a maximum of 2 hours until used in part B.

B. 3-Chloro-4-fluorobenzaldehyde

To a stirred mixture of hydrated copper sulfate 20 g and anhydrous sodium sulfate 3.1 g in a 10% formaldoxime solution (1.14 mole) was added rapidly a mixture of fused sodium acetate 500 g in water (560 ml). The resultant green reaction mixture was chilled and maintained at 10°–15° by means of an ice bath. The diazonium salt solution prepared in part A was introduced below the surface of the green followed by continued stirring for 1 hour. The 18° reaction mixture was treated with concentrated hydrochloric acid (720 ml) and then heated at reflux for 2 hours. After the crude aldehyde was isolated by steam distillation the 6 l. of distillate was extracted with 3 × 1 l. portions of ether. The ethereal extracts were combined and the treated with 1 l. of saturated sodium bicarbonate solution to a pH of 6. The ethereal layer was separated and then concentrated in vacuo to give 55 g (45%). The crude intermediate was used without further purification in part C.

C. 3-Chloro-4-fluorocinnamic acid

A stirred mixture of 3-chloro-4-fluorobenzaldehyde (55 g, 0.35 mole), malonic acid (47 g, 0.45 mole) and 3.5 ml of piperidine in 138 ml of pyridine was heated on a steam bath for 2 hours. The reaction solution was poured into a mixture of 200 ml of concentrated hydrochloric acid and 320 g of ice to give after filtration and water wash 44 g (63%). The crude intermediate was used without further purification in part D.

D. 1-(3-Chloro-4-fluorocinnamamido)hydantoin

To 44 g (0.22 mole) of 3-chloro-4-fluorocinnamic acid was added dropwise thionyl chloride (250 ml) followed by heating at reflux for 2 hours. The excess thionyl chloride was removed in vacuo and the residue remaining flushed with dry benzene. The reaction residue was chilled on an ice bath followed by the rapid addition of 1-aminohydantoin hydrochloride (33 g, 0.22 mole). To the cold reaction mixture was added dropwise pyridine (250 ml). After the addition was complete the cold reaction mixture was heated on a steam btah for 3 hours then poured into 3.5 l. of HCl/ice. Upon standing at room temperature overnight the acidic reaction mixture was filtered and washed with water to give 54 g (82%).

The analytical sample was prepared by one recrystallization from $CH_3NO_2$ (DARCO) m.p. 258°–260°.

Anal. Calcd. for $C_{12}H_9ClFN_3O_3$: C, 48.42; H, 3.05; N, 14.12. Found: C, 48.45; H, 3.18; N, 14.04.

What is claimed is:

1. A compound of the formula:

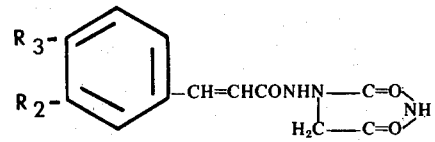

wherein $R_2$ is a member of the group consisting of hydrogen, chloro, fluoro and trifluoromethyl; $R_3$ is a member of the group consisting of hydrogen, chloro, fluoro, methyl, ethyl and cyano; and $R_2$ and $R_3$ taken together are methylenedioxy.

2. The compound 1-(3,4-dichlorocinnamamido)hydantoin.
3. The compound 1-cinnamamidohydantoin.
4. The compound 1-(3-chloro-4-methylcinnamamido)hydantoin.
5. The compound 1-(4-chlorocinnamamido)hydantoin.
6. The compound 1-(3,4-methylenedioxycinnamamido)hydantoin.
7. The compound 1-(4-chloro-3-trifluoromethylcinnamamido) hydantoin.
8. The compound 1-(4-fluorocinnamamido)hydantoin.
9. The compound 1-(3-chloro-4-ethylcinnamamido)hydantoin.
10. The compound 1-(4-cyanocinnamamido)hydantoin.
11. The compound 1-(3-fluorocinnamamido)hydantoin.
12. The compound 1-(3-chloro-4-fluorocinnamamido)hydantoin.

* * * * *

UNITED STATES PATENT OFFICE
CERTIFICATE OF CORRECTION

Patent No. 3,931,168     Dated January 6, 1976

Inventor(s) Robert J. Alaimo and Christopher J. Hatton

It is certified that error appears in the above-identified patent and that said Letters Patent are hereby corrected as shown below:

The structural formula in column 1 and Claim 1 should be:

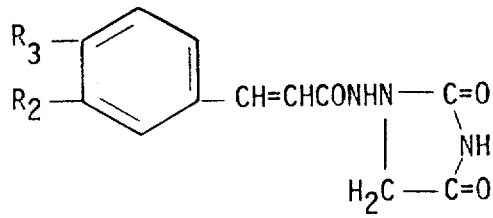

Signed and Sealed this first Day of June 1976

[SEAL]

Attest:

RUTH C. MASON
*Attesting Officer*

C. MARSHALL DANN
*Commissioner of Patents and Trademarks*